(12) United States Patent
Nord et al.

(10) Patent No.: US 8,027,430 B2
(45) Date of Patent: Sep. 27, 2011

(54) SYSTEMS AND METHODS FOR ADAPTING A MOVEMENT MODEL BASED ON AN IMAGE

(75) Inventors: Janne Ilmari Nord, Espoo (FI); Jarkko Yrjänä Peltola, Tuusula (FI)

(73) Assignee: Varian Medical Systems International AG, Zug (CH)

(*) Notice: Subject to any disclaimer, the term of this patent is extended or adjusted under 35 U.S.C. 154(b) by 910 days.

(21) Appl. No.: 11/830,732

(22) Filed: Jul. 30, 2007

(65) Prior Publication Data
US 2009/0034819 A1 Feb. 5, 2009

(51) Int. Cl.
*A61N 5/10* (2006.01)
*A61B 6/03* (2006.01)
*A61B 5/05* (2006.01)
*A61B 5/08* (2006.01)
*A61B 5/103* (2006.01)
*A61B 5/113* (2006.01)

(52) U.S. Cl. ............ 378/65; 378/62; 600/416; 600/427; 600/429; 600/534

(58) Field of Classification Search .............. 378/62–65, 378/68, 69, 95, 97, 108, 165; 600/425–429, 600/407, 410, 411, 415–417, 436, 484, 529, 600/531–543
See application file for complete search history.

(56) References Cited

U.S. PATENT DOCUMENTS

| | | | |
|---|---|---|---|
| 5,398,684 A | 3/1995 | Hardy | |
| 5,818,902 A | 10/1998 | Yu | |
| 6,907,105 B2 | 6/2005 | Otto | |
| 7,124,041 B1 | 10/2006 | Johnson et al. | |
| 7,162,008 B2 | 1/2007 | Earl et al. | |
| 7,184,814 B2 | 2/2007 | Lang et al. | |
| 7,239,908 B1 | 7/2007 | Alexander et al. | |
| 7,333,591 B2 | 2/2008 | Earl et al. | |
| 7,596,283 B2 * | 9/2009 | Xu et al. | 382/294 |
| 7,933,380 B2 * | 4/2011 | Nord et al. | 378/65 |

(Continued)

FOREIGN PATENT DOCUMENTS

WO 0007668 A1 2/2000

(Continued)

OTHER PUBLICATIONS

Rongping Zent et al, "Estimating 3-D Respiratory Motion from Orbiting Views by Tomographic Image Registration," IEEE Transactions on Medical Imaging, IEEE Service Center, Piscataway, NJ, US, voL. 26, No. 2, Feb. 1, 2007, pp. 153-163, XP011161757, ISSN: 0278-0062.

(Continued)

*Primary Examiner* — Anastasia S. Midkiff
(74) *Attorney, Agent, or Firm* — Fitch Even Tabin & Flannery (57) ABSTRACT

Various embodiments of the invention include systems and methods for adapting a movement model based on an image captured during radiation treatment of a patient. The movement model may, for example, be used in radiotherapy to treat lung cancer. The movement model is typically based on a series of images of a patient captured over a period of time. The movement model and/or one or images included therein may be used to generate a reference image of the patient. The reference image is compared with an image of the patient optionally captured during treatment. The result of this comparison is used to adapt the movement model to conditions during the treatment.

32 Claims, 5 Drawing Sheets

U.S. PATENT DOCUMENTS

| | | | |
|---|---|---|---|
| 2004/0019274 A1* | 1/2004 | Galloway et al. | 600/425 |
| 2004/0184578 A1 | 9/2004 | Nakano | |
| 2006/0074292 A1* | 4/2006 | Thomson et al. | 600/411 |
| 2006/0256915 A1 | 11/2006 | Otto et al. | |
| 2007/0041494 A1* | 2/2007 | Ruchala et al. | 378/65 |
| 2007/0041495 A1* | 2/2007 | Olivera et al. | 378/65 |
| 2007/0041497 A1* | 2/2007 | Schnarr et al. | 378/65 |
| 2007/0043286 A1* | 2/2007 | Lu et al. | 600/407 |
| 2008/0031404 A1* | 2/2008 | Khamene et al. | 378/6 |
| 2008/0144772 A1 | 6/2008 | Yi et al. | |
| 2008/0226030 A1 | 9/2008 | Otto | |
| 2008/0298550 A1 | 12/2008 | Otto | |

FOREIGN PATENT DOCUMENTS

| | | |
|---|---|---|
| WO | 2008011725 A1 | 1/2008 |

OTHER PUBLICATIONS

Rongping Zent et al, "Respiratory Motion Estimation from Slowly Rotating X-Ray Projections: Theory and Simulation," Medical Physics, AIP, Melville, NY, US, voL. 32, No. 4, Mar. 18, 2005, pp. 984-991, XP012075320, ISSN: 0094-2405.

Hawkes D J et al, "Motion and Biomechanical Models for Image-Guided Interventions," Biomedical Imaging: From Nano to Macro, 2007, ISBI 2007, 4th IEEE International Symposium on, IEEE, PI, Apr. 1, 2007, pp. 992-995, ZXP031084443, ISBN: 978-1-4244-0671-5.

Thirion, Jean-Philippe, "Non-Rigid Matching Using Demons," Proceedings of the 1996 Conference on Computer Vision and Pattern Recognition (CVPR '96), San Francisco, Jun. 18-20, 1996, IEEE Computer Society, Washington, DC, USA, pp. 245-251, ISBN: 0-8186-7258-3.

Lester, H. et al., "Non-linear registration with the variable viscosity fluid algorithm," Proceedings of the 16th International Conference on Information Processing in Medical Imaging, Lecture Notes in Computer Science, Springer-Verlag, UK, vol. 1613, pp. 238-251, 1999, ISBN: 3-540-66167-0.

M A Earl et al., "Inverse planning for intensity-modulated arc therapy using direct aperture optimization," 2003, 1075-1089, vol. 48, IOP Publishing Ltd, UK.

Stefanescu, R. et al., "Grid powered nonlinear image registration with locally adaptive regularization, "Medical Image Analysis, Oxford University Press, GB, vol. 8, (2004), pp. 325-342.

Alankus, Gazihan, "Animating Character Navigation Using Motion Graphs," A Thesis submitted to the Graduate School of Natural and Applied Sciences of Middle East Technical University; Jun. 2005, 32 pages.

Wang, H. et al., "Validation of an accelerated 'demons' algorithm for deformable image registration in radiation therapy," Physics in Medicine and Biology, Taylor & Francis Ltd., London, GB, vol. 50, No. 12, Jun. 2005, pp. 2887-2905.

Shen, Jian-Kun et al., "Deformable Image Registration," Image Processing, ICIP 2005, IEEE International Conference, Sep. 11-14, 2005, IEEE, vol. 3, pp. 1112-1115, ISBN 978-0-7803-9134-9/05.

Wilkie, K. P. et al., "Mutual Information-Based Methods to Improve Local Region-of-Intrest Image Registration," Image Analysis and Recognition Lecture Notes in Computer Science; LNCS, Springer, Berlin, DE, vol. 3656, Sep. 28, 2005, pp. 63-72, XP019020206, ISBN: 978-3-540-29069-8, abstract, section 3.1.

Daliang Cao et al., "Continuous intensity map optimization (CIMO): A novel approach to leaf sequencing in step and shoot IMRT," Medical Physics, Apr. 2006, 859-867, vol. 33 No. 4, American Association of Physicists in Medicine.

D.M. Shepard et al, "An arc-sequencing algorithm for intensity modulated arc therapy," Feb. 2007, 464-470, vol. 34 No. 2, American Association of Physicists in Medicine.

Chao Wang et al., "Arc-modulated radiation therapy (AMRT): a single-arc form of intensity-modulated arc therapy," Phys. Med. Biol., 2008, pp. 6291-6303, vol. 53, Institute of Physics and Engineering in Medicine, Printed in UK.

* cited by examiner

SYSTEMS AND METHODS FOR ADAPTING A MOVEMENT MODEL BASED ON AN IMAGE

CROSS-REFERENCES TO RELATED APPLICATIONS

This nonprovisional U.S. patent application is related to nonprovisional U.S. patent application Ser. No. 11/726,884 filed Mar. 23, 2007 and entitled "Image Deformation Using Multiple Image Regions," Ser. No. 11/804,693 filed May 18, 2007 and entitled "Leaf Sequencing," and Ser. No. 11/804,145 filed May 16, 2007 and entitled "Compressed Movement Model." The disclosures of these patent applications are hereby incorporated herein by reference.

BACKGROUND

1. Field of the Invention

The invention is in the field of medical imaging and more specifically in the field of modeling movements of a patient during treatment.

2. Related Art

Currently, to prepare a treatment plan for a patient, a model of the patient's routine movements may be generated. For example, to treat lung cancer, a model of the patient's breathing may be generated prior to radiation therapy. By modeling these movements, the treatment may be more efficiently delivered to the diseased areas by adjusting the delivery of the radiation according to the breathing movements of the patient. Thus, the patient may receive more radiation in targeted areas and be exposed to less radiation in healthy tissues.

Images of the patient, such as a lung, may be generated during treatment. However, these images are not typically sufficient in number or quality to calculate a movement model during the treatment itself. Movement models are, therefore, prepared some time before the treatment. Unfortunately, due to progression of a cancer, positioning of the patient, and/or other factors, the previously generated movement model may be less accurate than desired at the time of the treatment. There is, therefore, a need for improvement modeling of the patient during treatment.

SUMMARY

Various embodiments of the invention include systems and methods for adapting a previously generated movement model to better estimate the movement of a patient during treatment. The adaptation is based on an image of the patient captured during treatment and, thus, may change the movement model so as to better reflect actual positions during treatment. Prior to treatment of the patient, a movement model of the patient is generated from a series of images of the patient captured over a period of time. The movement model comprises two or more deformation fields that are each associated with different points in time. Each of the deformations fields comprises a plurality of displacement vectors indicating a movement of the patient. Methods of generating movement models are known in the art.

Adaptation of the movement model is based on a comparison of an image captured during treatment to a reference image optionally generated from the movement model. In some embodiments, the reference image comprises an average image of the patient over a period of time prior to the treatment. In some embodiments, the reference image is derived from one or more of the images used to generate the movement model prior to treatment. In some embodiments, the reference image is an image obtained over a time period contemporaneous with a time period during which images used to generate the movement model were obtained.

The comparison between the image captured during treatment and the reference image results in a model adaptation field. The model adaptation field is a field configured for adapting a movement model to real-time conditions of a patient. The model adaptation field is similar to deformation fields in that it comprises a plurality of vectors indicating differences in location. However, the differences represented by the model adaptation field are those differences found between the reference image and the captured image.

During treatment, the model adaptation field is used to adapt the movement model to more accurately reflect movement of the patient. For example, in some embodiments, the vectors within the deformation fields of the movement model are adjusted, on a vector by vector basis, using corresponding vectors within the model adaptation field. In some embodiments, the vectors within the deformation fields are adjusted using an average or some other function of the vectors within the model adaptation field. The adapted movement model is then typically stored in a memory and/or processed to generate a representation of the estimated movement of the patient. This estimated movement may then be used to guide radiation delivery.

In some embodiments, the movement model is generated by capturing a series of images from a patient and then adapted using an image captured during treatment of the same patient. Alternatively, the movement model may be generated by capturing images from one or more patients other than the patient that is treated using the adapted movement model. For example, the movement model may be generated using images received from multiple patients and then adapted using the systems and methods described herein in order to better guide the treatment of a specific patient. In various embodiments, the movement model is generated using the systems and methods disclosed in U.S. patent application Ser. No. 11/726,884 filed Mar. 23, 2007 and entitled "Image Deformation Using Multiple Image Regions;" Ser. No. 11/804,693 filed May 18, 2007 and entitled "Leaf Sequencing;" and Ser. No. 11/804,145 filed May 16, 2007 and entitled "Compressed Movement Model."

In various embodiments, the movement model is adapted by first dividing the movement model into more than one phase, each phase including one or more deformation fields. A different reference image is then generated for each phase. These reference images are then compared to one or more images captured in corresponding phases during treatment of a patient. Each comparison results in a phase specific model adaptation field that can be used to adjust the movement model on a phase specific basis. In a similar manner, the movement model may be adapted by first dividing the movement model into more than one region and adjusting the movement model on a region specific basis.

Various embodiments of the invention include a method comprising receiving a movement model of a patient, the movement model generated prior to the start of a treatment session and comprising a plurality of deformation fields each associated with a different point in time, receiving a reference image based on the movement model, capturing a treatment image of the patient, calculating a model adaptation field representative of a difference between the reference image and the treatment image, the model adaptation field comprising a plurality of deformation vectors each representing change in location, and adapting the movement model using the model adaptation field.

Various embodiments of the invention include a method comprising receiving a movement model based on movement of a first patient, generating a reference image based on the movement model associated with the first patient, generating an image of a second patient during a treatment session, comparing the reference image and the treatment image to generate a model adaptation field, and using the model adaptation field to adapt the movement model for treatment of the second patient.

Various embodiments of the invention include a system comprising a simulation module configured to generate a first image based on a movement model, a model deformation field module configured to receive a second image and generate a model adaptation field representative of differences between the first image and the second image, the second being captured during a treatment session, and an adaptation module configured to adapt the movement model using the model adaptation field.

DETAILED DESCRIPTION

A movement model used in a medical treatment is adapted to adjust for differences between conditions under which the movement model was developed and conditions under which the movement model is used for treatment. These differences may result from, for example, patient movement, change in patient orientation, change in medical status, change in patient identity, change in cancer distribution, and/or the like. For example, in the treatment of colon cancer, radiation therapy may be targeted at affected colon tissue. However, as the result of natural digestive processes, this colon tissue may move prior to or during treatment. This movement, if not compensated for, may affect the efficacy and/or accuracy of the treatment.

The movement model is typically generated from one or more series of images of the patient captured over a period of time. For example, images of the lungs may be captured over several breathing cycles, or images of the digestive system may be captured over several days. The period of time is optionally divided into different phases and these phases may be adapted separately or in a weighted fashion.

The movement model is typically generated before the treatment begins because capturing the required images and generating the movement model from those images can take some time. It may be preferable not to occupy a treatment system for this time. Thus, in some embodiments, the images used for generating the movement model are captured at a different location than that at which treatment is provided. Further, the position of a patient may change over a short period of time. For example, a patient's breathing may cause a change in the position of a tumor in the patient's chest or abdomen, or the patient may voluntarily or inadvertently move during treatment. In some embodiments, the systems and methods discussed herein are used to adapt a movement model to real-time changes in patient position. The movement model may be adapted more than one time during a specific treatment session. A treatment session is considered to begin when a patient is positioned to receive therapeutic radiation. This positioning typically occurs on a support such as a gurney, platform, chair, or the like. A treatment session is considered to end when the patient leaves the treatment area.

The images used to generate the movement model may also be used by a radiologist, physician, technician, expert system, or the like, to plan a treatment. When this occurs, the delay between capturing these images and the beginning of treatment may be several minutes, hours or days. In various embodiments, the images used to generate the movement model are captured more than 1, 2, 5, 10, 30, 60, or 120 minutes before the start of treatment. As is described further herein, the reference image may be one of the images used to generate the movement model or may be a derivative of two or more of the images used to generate the movement model. This derivative may be a weighted average, combination, sum, result of a statistical analysis, and/or the like.

According to various embodiments, an image to be compared to the reference image is captured between the start of treatment and the delivery of radiation, and/or is captured after the delivery of radiation starts. This image is referred to herein as the treatment image. For example, in some embodiments, a first treatment image is captured prior to the start of radiation delivery and a second treatment image is captured between the start of radiation delivery and the end of radiation delivery. A treatment may include more than one dosage of radiation separated in time by acquisition of a treatment image and adaptation of a movement model.

Figure 1:
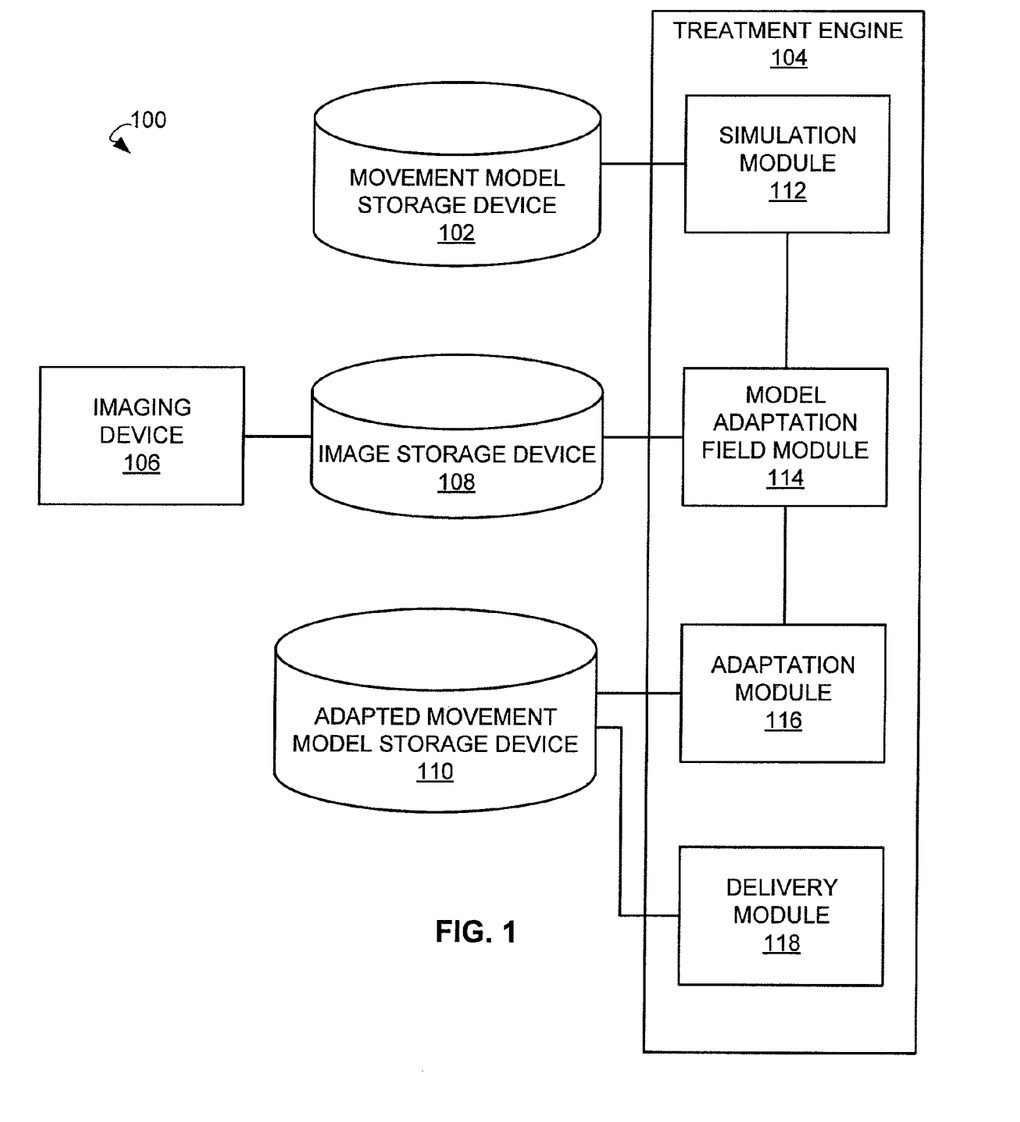
FIG. 1 depicts part of a radiation treatment system, according to various embodiments of the invention.

FIG. 1 depicts part of a radiation treatment system 100, according to various embodiment of the invention. The radiation treatment system 100 comprises a movement model storage device 102, a treatment engine 104, an optional imaging device 106, an image storage device 108, and an optional adapted movement model storage device 110. The treatment engine 104 further comprises a simulation module 112, a model adaptation field module 114, an adaptation module 116, and a delivery module 118.

The movement model storage device 102, the treatment engine 104, the image storage device 108, and the adapted movement model storage device 110 may comprise one or more computing devices including computer readable media, a processor, and logic embodied in hardware, software, and/or firmware. The computer readable medium may be configured to store instructions executable by a processor, images, fields, and/or the like. For example, the treatment engine 104 may comprise a computing device having a processor configured to execute computing instructions stored in a random access memory and/or a hard drive. These instructions may be divided into the simulation module 112, the model deformation field module 114, the adaptation module 116 and the delivery module 118. These modules may share some instructions.

The movement model storage device 102 is configured to store a movement model. This storage may be temporary, e.g., in working memory, or more permanent. In various embodiments, movement model storage device 102 comprises a hard drive, an optical drive, random access memory, volatile memory, nonvolatile memory, and/or the like. The movement model may comprise, for example, one or more images, and one or more deformation fields each associated with a different point in time. The movement model may also comprise one or more interpolation fields. In various embodiments, the movement model is generated according to the systems and methods disclosed in U.S. patent application Ser. No. 11/726,884 filed Mar. 23, 2007 and entitled "Image Deformation Using Multiple Image Regions." In alternative embodiments, other movement models, generated using other modeling techniques, may be stored in the movement model storage device 102.

The simulation module 112 is configured to access the movement model stored in the movement model storage device 102 and/or generate a reference image. The reference image may comprise an average, or other statistical analysis, of an image of the patient included in the movement model. Alternatively, the reference image may be an image that is not included in the movement model but was captured at approximately the time during which images for generation of the movement model were captured. The reference image may be captured over a period of time, e.g., be a time averaged image. The reference image may be calculated using various known techniques for averaging multiple images and/or deformation fields. In embodiments where an image is used directly as a reference image without modification or processing, the simulation module 112 may simply read the reference image from memory such as movement model storage device 102.

According to some embodiments, the simulation module 112 generates one or more reference images by dividing the movement model into one or more phases. Images within each phase may then be averaged to generate a phase specific reference image. Optionally, each of the phases is assigned a weight. In some embodiments, the weight associated with all of the phases may be the same. In other embodiments, the weights may be different. For example, a weight may represent the probability of a given movement occurring at any particular time. These probabilities may be measured during treatment using an x-ray imaging device and/or a camera configured to capture visual images of the patient.

In some embodiments, a reference image is then generated by calculating a weighted average of the phase specific reference images. The reference image is thus a weighted average image of the patient over the period of time during which the series of images (of the movement model) was captured. Alternatively, each phase specific reference image may be used to adapt a different phase of the movement model.

The optional imaging device 106 is configured to capture a treatment image of the patient during treatment. The imaging device 106 may comprise, for example, a computed tomography scanner, an x-ray source, an ultrasound imager, a magnetic resonance imaging device, an x-ray detector, and/or the like. The imaging device 106 may capture the treatment image on a short timescale, e.g., less than 1, 3 or 5 seconds. Alternatively, the imaging device 106 may capture the treatment image on a longer time scale, e.g., longer than 5, 15, 30 or 60 seconds. Thus, the captured image may be a time averaged image of the patient over multiple movement cycles, e.g., multiple respiratory cycles. Time averaging can be accomplished by averaging images taken over short timescales or by capturing an image over a longer timescale, e.g., collecting x-ray data semi-continuously for 60 seconds. Typically, the treatment image is captured such that it can be compared to a reference image. For example, if the reference image is representative of a patient's breathing for two minutes, then the treatment image may be an average over the same timescale. In embodiments where weights associated with phase images are measured during treatment, the imaging device 106 may comprise a visible or infrared wavelength camera configured to capture still and/or video images of the patient. These images may be used to calculate weights of specific phases by measuring an amount of time spent in each movement phase. The image storage device 108 is configured to store the captured images. Imaging device 106 is optional where another image source is available.

The model adaptation field module 114 is configured to compare the reference image generated or retrieved by the simulation module 112 to the treatment image captured during treatment. To compare the images, the model adaptation field module 114 performs a deformable image registration between the reference image and the treatment image. The deformable image registration results in a deformation field representative of differences between the images. Methods of performing deformable image registration are known in the art. One method of performing deformable image registration is disclosed in U.S. patent application Ser. No. 11/726,884 filed Mar. 23, 2007 and entitled "Image Deformation Using Multiple Image Regions." This deformation field is referred to herein as a model adaptation field because it may be used to adapt a movement model to patient conditions (e.g., position and movement rate) during treatment.

The adaptation module 116 is configured to adapt the movement model using the model adaptation field calculated by the model adaptation field module 114. In some embodiments, the adaptation module 116 adapts the movement model by applying the model adaptation field to each deformation field within the movement model. The model adaptation field is applied by adjusting the vectors of the deformation field using the vectors of the model adaptation field. These vectors may be applied on either an individual vector basis or on an aggregate basis. For example, on an individual vector basis, a vector of the model adaptation field is added to a vector of the deformation field. In an aggregate basis, an average of a set of the vectors of the model adaptation field is added to the each vector of the deformation field. Methods of adapting a movement model using the model adaptation field are discussed further elsewhere herein, for example in the discussion of FIG. 3.

The adapted movement model storage device 110 is configured to store the movement model as adapted by the adaptation module 116. In some embodiments, the adapted movement model storage device 110 shares memory with the movement model storage device 102 and/or image storage device 108.

The adapted movement model stored in the adapted movement model storage device 110 is accessed by the delivery module 118. In some embodiments, the delivery module 118 includes systems for delivering radiation to a patient based on the adapted movement model. These systems may include, for example, a gantry, an x-ray or particle beam source, a patient support, and/or the like. In some embodiments, the delivery module 118 includes logic configured to determine a treatment plan for delivery of radiation to a patient. This logic may include, for example, the logic disclosed in nonprovisional U.S. patent application Ser. No. 11/804,693 filed May 18, 2007 and entitled "Leaf Sequencing." In some embodiments, the delivery module 118 comprises an interface configured for communicating the adapted movement model to a system external to radiation treatment system 100. In these embodiments, delivery of therapeutic radiation may be accomplished using the external system.

Figure 2:
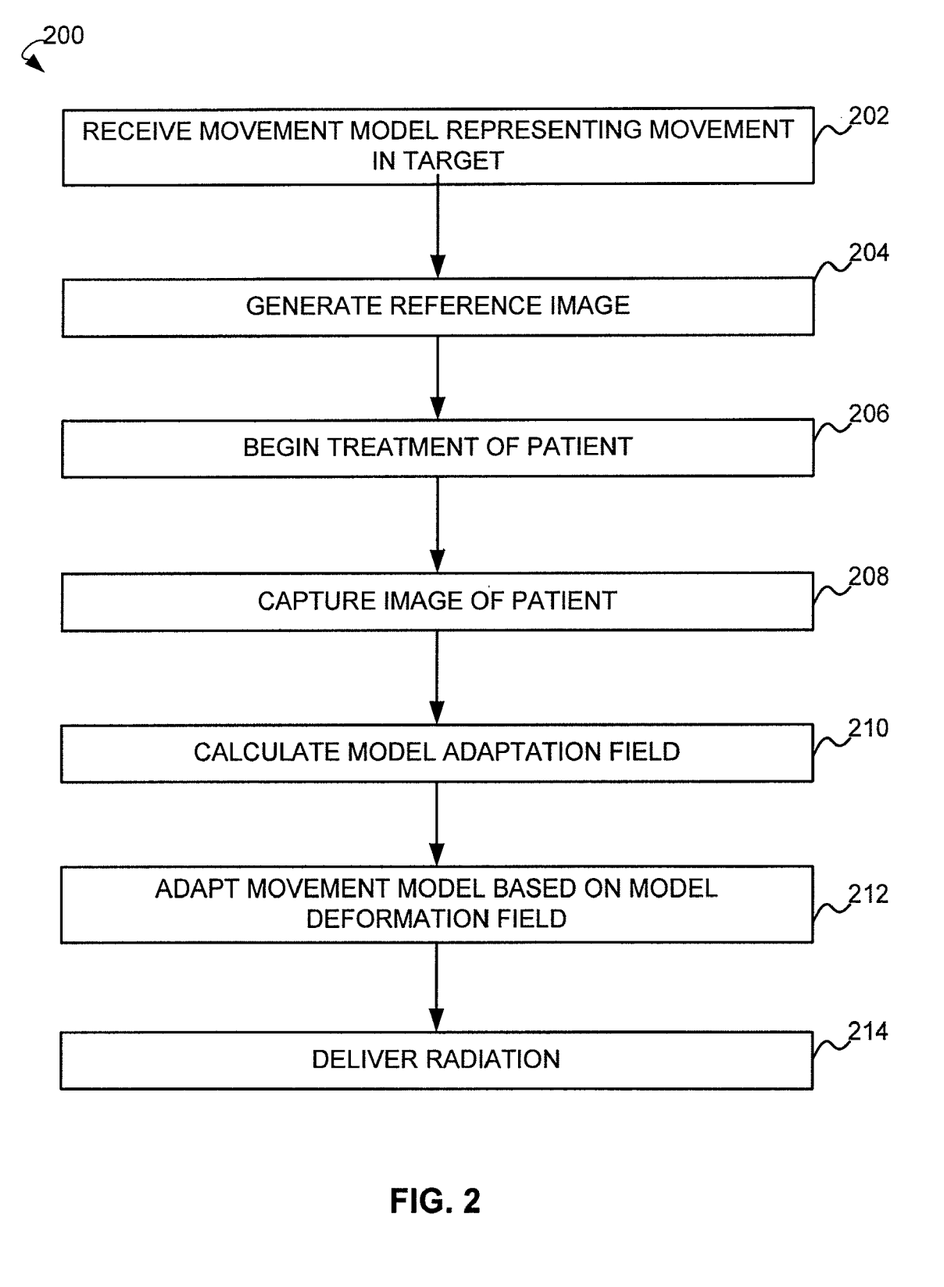
FIG. 2 is a flowchart illustrating a method of adapting a movement model, according to various embodiments of the invention.

FIG. 2 is a flowchart illustrating a method 200 of adapting a movement model, according to various embodiments of the invention. The method 200 is optionally performed using the radiation treatment system 100 as described herein.

In a step 202, a movement model representing movement of a patient is received. The received movement model may be generated by a system external to radiation treatment system 100, or using imaging device 106 and logic (not shown) within radiation treatment system 100. According to various embodiments, the movement model may represent movements including, but not limited to, respiratory movements, cardiac movements, digestive movements, eye movements, involuntary movements, and/or voluntary movements. In some embodiments, the received movement model is spatially divided, each division representative of a portion of a patient and characterized by distinct movement characteristics. In some embodiments, the received movement model is temporally divided into different phases. A movement model may be both temporally and spatially divided. The movement model received in step 202 is typically generated prior to the start of a treatment session.

In a step 204, the simulation module 112 is used to generate a reference image of the patient. In some embodiments, the reference image is read from the movement model storage device 102. In some embodiments, the reference image is extracted from the movement model received in step 202. In some embodiments, the reference image is calculated based on images and/or deformation fields included within the movement model received in step 202. For example, the reference image may be an average of images within the movement model. These images may be stored in the movement model or may be derivable using stored images and deformation fields, see for example, the calculation of interpolated deformation fields in U.S. patent application Ser. No. 11/804,145 filed May 16, 2007 and entitled "Compressed Movement Model."

In an optional step 206, the treatment of the patient begins. This treatment includes positioning the patient for delivery of radiation, e.g., x-rays or particles. For example, the patient may be positioned on a gurney. Typically, part of the treatment is based on the adapted movement model generated in a step 212 discussed elsewhere herein.

In a step 208, at least one treatment image of the patient is captured using image device 106. The treatment image may comprise a time averaged image over a plurality of movement cycles. According to various embodiments, the treatment image is two dimensional, three dimensional or four dimensional. Step 208 is typically performed after the start of a treatment session. More than one reference image may be captured, for example, if the movement model is spatially or temporally divided.

In a step 210, a model adaptation field is calculated. Step 210 may comprise performing a deformable image registration between the reference image generated in step 204 and the treatment image captured in step 208. The model adaptation field may then be calculated based on the registered images. If the movement model is spatially or temporally divided, then a different deformable image registration may be performed for each division.

In the step 212, the movement model received in step 202 is adapted based on the model adaptation field calculated in step 210. One method used to perform the adaptation is described elsewhere herein, for example in connection with FIG. 3. If the movement model is spatially or temporally divided, then a different adaptation may be performed for each division.

In an optional step 214, radiation is delivered to the patient. This radiation can include x-rays, particles, and/or the like. The radiation is optionally delivered according to a treatment plan based on the adapted movement model. In alternative embodiments, step 214 begins prior to steps 208, 210 or 212. If step 214 occurs prior to step 212, then radiation delivery may start using the unaltered movement model. After the step 212 is completed, the current treatment plan and thus the ongoing radiation delivery may be altered to use the adapted movement model. Thus, a treatment in progress is altered using the method 200. In some embodiments, steps 208 through 212 are repeated more than once during a treatment session, each repetition being configured to further adapt a movement model received in step 202 to the movement of a patient. Thus, if step 210 is performed more than one time, then the calculation of the model deformation field can be based on either the movement model received in step 202 or on a previously adapted version of this movement model.

Figure 3:
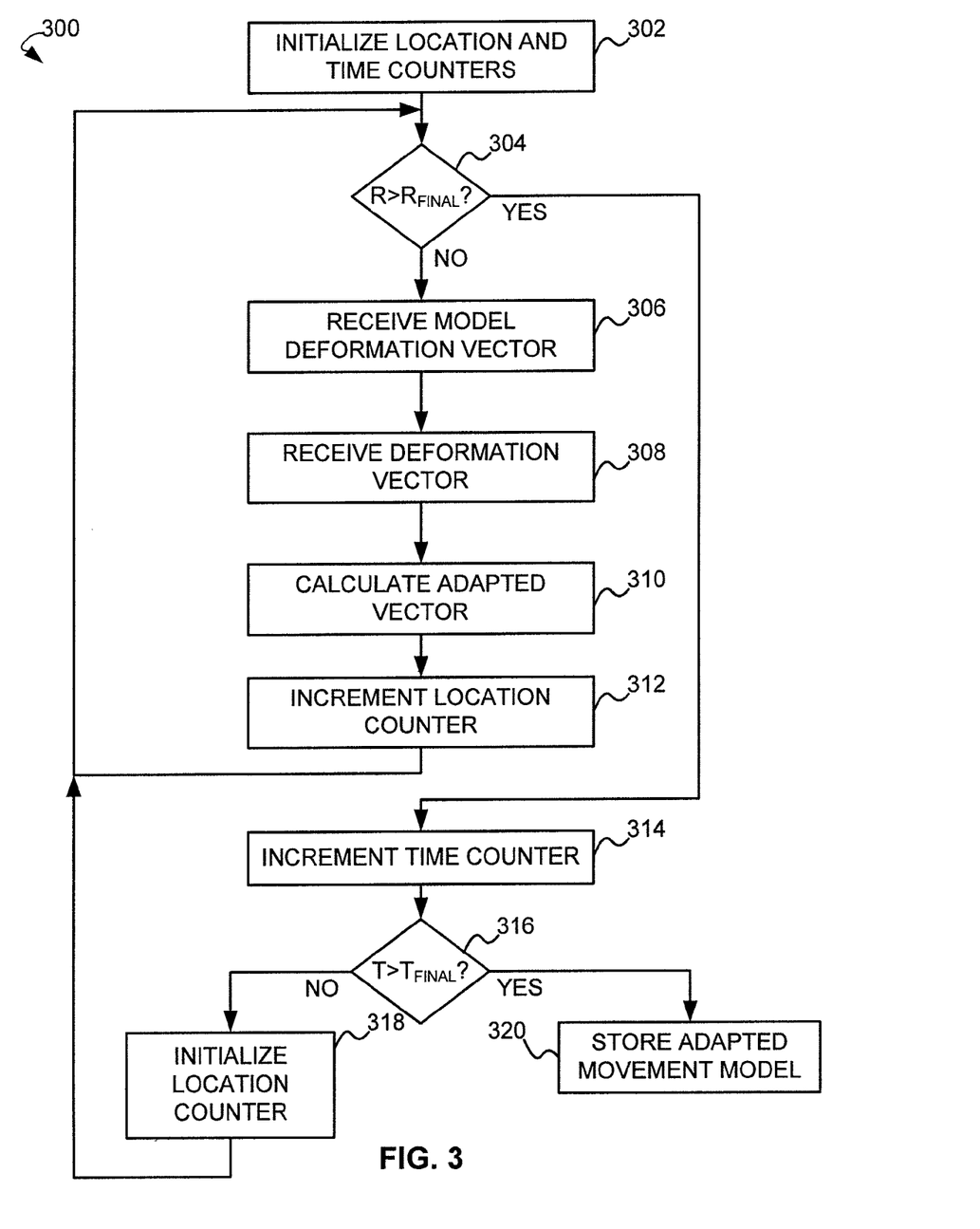
FIG. 3 is a flowchart illustrating a method of calculating an adapted movement model, according to various embodiments of the invention.

FIG. 3 is a flowchart illustrating a method 300 of calculating an adapted movement model, according to various embodiments of the invention. The method 300 is optionally performed by the adaptation module 116 and/or as part of the step 212 of method 200. The movement model may comprise a plurality of deformation fields and/or images that are each indicative of the movement and/or position of the patient at a different point in time. The movement model may be three or four dimensional, one of the dimensions being time.

The deformation fields of the movement model each comprise at least one vector indicating a direction and magnitude of the movement of a location within the patient. The deformation fields and/or the vectors within the deformation fields may represent two dimensional or three dimensional movements. Each of the locations and points in time may be represented by a position counter and time counter, respectively. For example, positions may be represented by values (0,0,0), (0,0,1), (0,0,2) . . . (x,y,z).

In a step 302, the values representing the locations (R) and the points in time (T) associated with the deformation field are initialized, e.g., set to zero. It is understood that the values described herein are exemplary; other methods for counting and/or incrementing the positions and the points in time may be used in other embodiments.

In a step 304, for each point in time ($T_N$), a determination is made as to whether a final position ($R_{FINAL}$) within the deformation field associated with the point in time has been exceeded.

If the final location has not been reached, (i.e., there are remaining unadapted vectors within the deformation field associated with the current time counter) a model deformation vector ($A_N$) within the model adaptation field at the location ($R_N$) is received in a step 306. The model deformation vector ($A_N$) is a vector in the model deformation field and represents the difference at position ($R_N$) between the reference image and the treatment image.

In a step 308, a deformation vector (B) at the location ($R_N$) and associated with a point in time ($T_N$) is received. The deformation vector (B) is a vector of the deformation field of the movement model and represents the movement of the patient at the location ($R_N$) at the point in time ($T_N$). In various embodiments, the deformation vector (B) is an unaltered vector from the movement model or a vector from a previously adapted version of the movement model.

In a step 310, an adapted vector is calculated. In some embodiments, the adapted vector is the sum of the vectors received in steps 306 and 308 (i.e., A+B). The adapted vector is an estimation of the movement at the location ($R_N$) within the patient at the point in time ($T_N$) based on the movement model and the treatment image.

In a step 312, the variable representing the location (R) is incremented such that the steps 304, 306, 308, and 310 are repeated with respect to each location (R) within the patient associated with an original deformation vector.

Returning to step 304, if each original deformation vector in the deformation field associated with a point in time has been corrected (e.g., if $R_N > R_{FINAL}$), the point in time (T) is incremented in a step 314. By incrementing the time counter, each of the deformation fields associated with the movement model may be adapted according to the model adaptation field.

In a step 316, a determination is made as to whether a final point in time ($T_{FINAL}$) has been exceeded. If the final point in time is not exceeded, the location variable is reinitialized in a step 318 and the steps 304, 306, 308, 310, and 312 are repeated with respect to the deformation field associated with the next point in time. If the final point in time is exceeded, the adapted movement model is stored in a step 320.

Figure 4A:
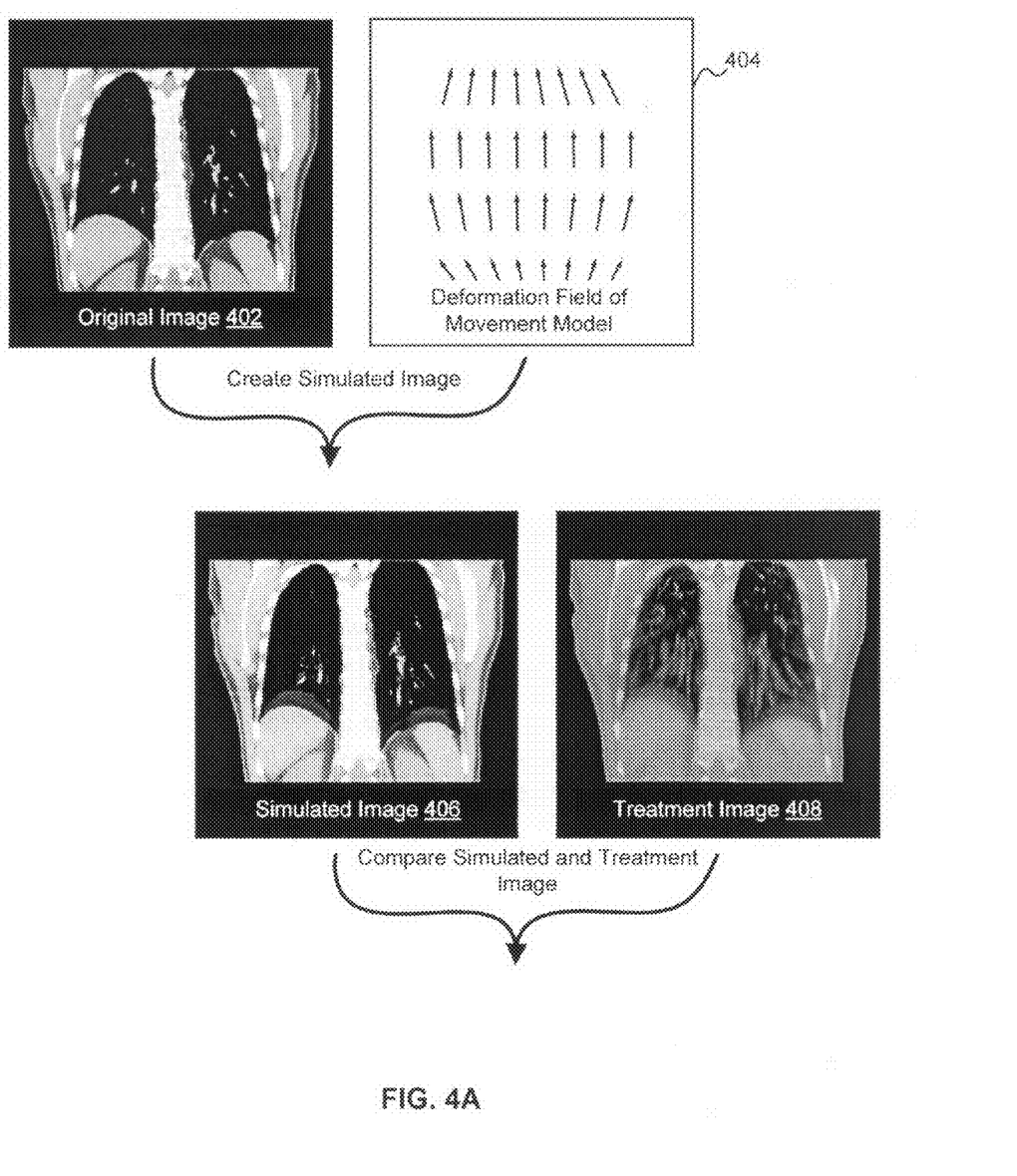
FIGS. 4A and 4B include a graphical representation of the adaptation of a movement model, according to various embodiments of the invention.
Figure 4B:
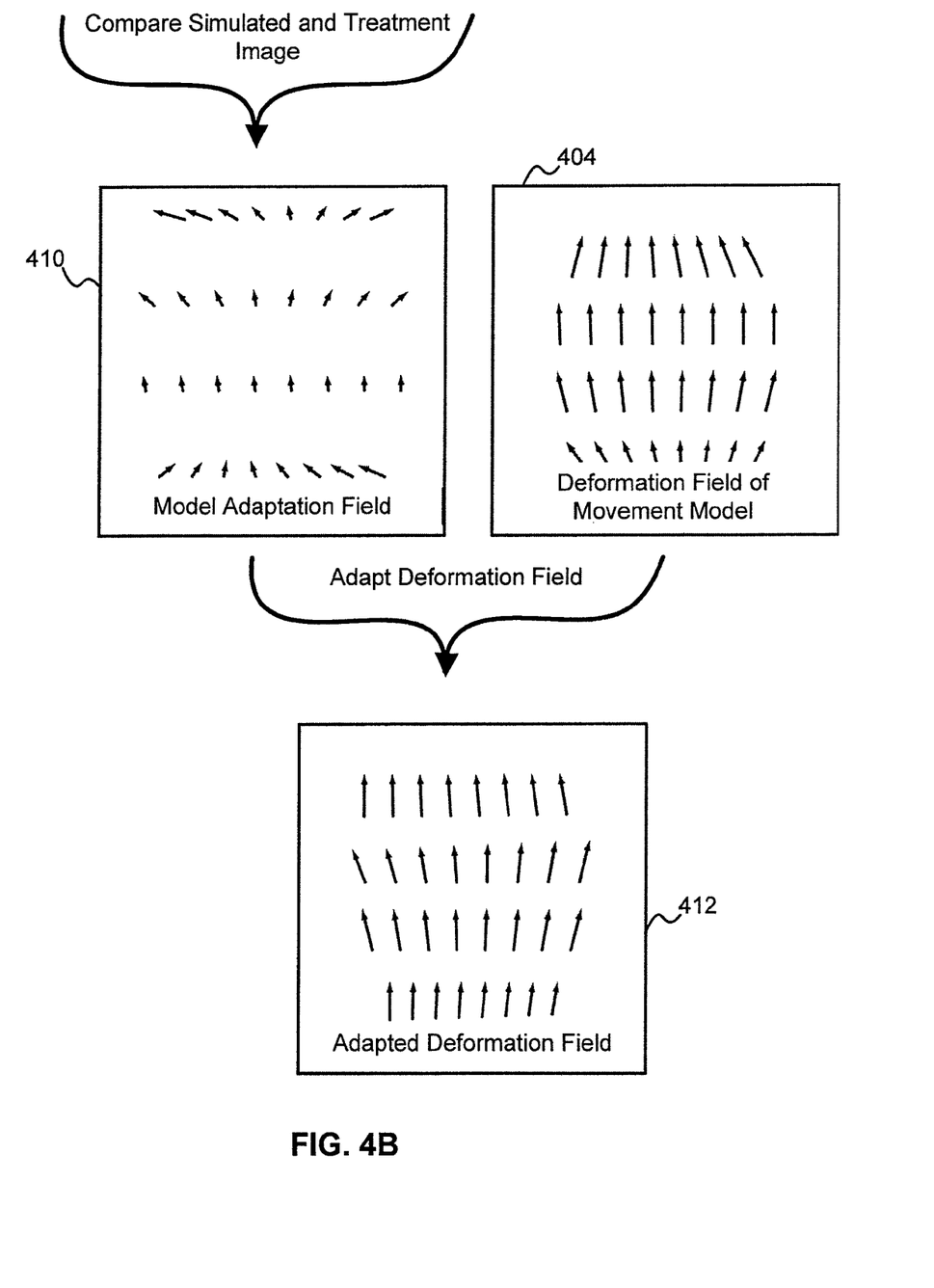

FIGS. 4A and 4B include a graphical representation of the adaptation of a movement model as may be accomplished using the method 200 of FIG. 2, according to various embodiments of the invention. In step 204 of method 200, an original image 402, such as an image stored with the movement model, and one or more original deformation fields in the movement model (e.g., original deformation field 404) are combined to generate a reference image, such as simulated image 406. In step 210 of FIG. 2 the simulated image 406 is compared with a treatment image 408 to generate a model adaptation field 410. Treatment image 408 is an image of the patient captured in step 206 of FIG. 2 after the start of treatment. The model adaptation field 410 is then used to adapt a deformation field 404 of the movement model in step 212 of FIG. 2. The result of this step is an adapted deformation field 412 of an adapted movement model.

Several embodiments are specifically illustrated and/or described herein. However, it will be appreciated that modifications and variations are covered by the above teachings and within the scope of the appended claims without departing from the spirit and intended scope thereof. For example, while respiratory movement and x-ray images are discussed herein by way of example, alternative embodiments of the invention may be used in relation to other types of movement and/or other types of images (e.g., ultrasound images, nuclear magnetic resonance images, or the like). Further, in some embodiments, the image captured in step 208 of FIG. 2 is used to correct artifacts in the original movement model or the adapted movement model calculated in step 212 of FIG. 2.

While the examples provided herein include beginning a treatment session prior to adapting a movement model, some embodiments of the invention include adapting a movement model prior to treatment. For example, a movement model generated based on data from more than one person may be adapted to better represent a specific patient prior to a treatment session.

The embodiments discussed herein are illustrative of the present invention. As these embodiments of the present invention are described with reference to illustrations, various modifications or adaptations of the methods and or specific structures described may become apparent to those skilled in the art. All such modifications, adaptions, or variations that reply upon the teachings of the present invention, and through which these teachings have advanced the art, are considered to be within the spirit and scope of the present invention. Hence, these descriptions and drawings should not be considered in a limiting sense, as it is understood that the present invention is in no way limited to only the embodiments illustrated.

What is claimed is:

1. A method comprising;
   receiving a movement model based on movement of a first patient;
   generating a reference image based on the movement model associated with the first patient;
   generating an image of a second patient during a treatment session;
   comparing the reference image and the treatment image to generate a model adaptation field; and
   using the model adaptation field to adapt the movement model for treatment of the second patient.

2. The method of claim 1, wherein the movement model is divided into a plurality of phases each representative of a phase of movement of the first patient.

3. The method of claim 2, wherein each of the plurality of phases is assigned a weight.

4. The method of claim 1, wherein the movement model is divided into a plurality of regions each representative of a different part of the first patient.

5. The method of claim 1, wherein receiving the movement model includes calculating the movement model based on images of the first patient.

6. The method of claim 1, wherein the received movement model is four dimensional.

7. The method of claim 1, wherein the movement model comprises a model of respiration of the first patient.

8. The method of claim 1, wherein the generated reference image comprises an image representative of the first patient over time.

9. The method of claim 1, wherein the treatment image is an x-ray image.

10. The method of claim 1, wherein the treatment session includes radiation delivery.

11. The method of claim 1, wherein comparing the reference image and the treatment image to generate a model adaptation field includes applying a deformable image registration algorithm to the reference image and the treatment image.

12. The method of claim 1, wherein using the model adaptation field to adapt the movement model for treatment of the second patient includes modifying a deformation field within the movement model.

13. The method of claim 1, further including repeating the steps of generating an image of the second patient and comparing the reference image to the treatment image to generate a model adaptation field at least a second time during the treatment session.

14. The method of claim 1, further including delivering radiation to the second patient using a treatment plan based on the adapted movement model.

15. The method of claim 1, wherein receiving the movement model includes receiving a movement model based on movement of a plurality of patients including the first patient.

16. A system comprising:
   a simulation module configured to generate a first image based on a movement model;
   a model deformation field module configured to receive a second image and generate a model adaptation field representative of differences between the first image and the second image, the second image being captured during a treatment session; and
   an adaptation module configured to adapt the movement model using the model adaptation field;
   wherein the movement model is based on movement of a first patient and the second image is representative of a position of a second patient.

17. The system of claim 16, wherein the first image is representative of movement of the first patient over time.

18. The system of claim 16, wherein the adaptation module is further configured to adapt the movement model more than one time during a treatment session.

19. The system of claim 16, further comprising an imaging device configured to capture the second image.

20. The system of claim 16, further comprising a delivery module configured to provide a radiation treatment based on the adapted movement model.

21. The system of claim 16, further comprising storage configured to store the adapted movement model.

22. The system of claim 16, further comprising logic configured to generate a treatment plan based on the adapted movement module.

23. The system of claim 16, wherein the movement model is divided into a plurality of phases, each representative of a phase of movement of the first patient.

24. The system of claim 23, wherein each of the plurality of phases is assigned a weight.

25. The system of claim 16, wherein the movement model is divided into a plurality of regions, each representative of a different part of the first patient.

26. The system of claim 16, wherein the movement model is four dimensional.

27. The system of claim 16, wherein the movement model comprises a model of respiration of the first patient.

28. The system of claim 16, wherein the first image comprises an image representative of the first patient over time.

29. The system of claim 16, wherein the second image is an x-ray image.

30. The system of claim 16, wherein the treatment session includes radiation delivery.

31. The system of claim 16, wherein the model deformation field module is further configured to apply a deformable image registration algorithm to the first and second images before generating the model adaptation field.

32. The system of claim 16, wherein the adaptation module is further configured to modify a deformation field within the movement model before adapting the movement model using the model adaptation field.

* * * * *